United States Patent
Turner et al.

(10) Patent No.: US 8,390,177 B2
(45) Date of Patent: *Mar. 5, 2013

(54) VIBRATING ELEMENT APPARATUS

(75) Inventors: Roy Colin Turner, Berkshire (GB); Barry Albert Snowdon, Berkshire (GB)

(73) Assignee: Mobrey Limited, Berkshire (GB)

( * ) Notice: Subject to any disclaimer, the term of this patent is extended or adjusted under 35 U.S.C. 154(b) by 5 days.

This patent is subject to a terminal disclaimer.

(21) Appl. No.: 12/919,095

(22) PCT Filed: Feb. 27, 2009

(86) PCT No.: PCT/US2009/001262
§ 371 (c)(1), (2), (4) Date: Aug. 24, 2010

(87) PCT Pub. No.: WO2009/110988
PCT Pub. Date: Sep. 11, 2009

(65) Prior Publication Data
US 2011/0001395 A1    Jan. 6, 2011

(30) Foreign Application Priority Data
Mar. 1, 2008 (GB) .................................. 0803899.4

(51) Int. Cl.
*H01L 41/053* (2006.01)

(52) U.S. Cl. .......................... 310/348; 310/324; 310/344

(58) Field of Classification Search .................. 310/328, 310/340, 344, 348, 324
See application file for complete search history.

(56) References Cited

U.S. PATENT DOCUMENTS

| 4,594,584 | A | * | 6/1986 | Pfeiffer et al. | 340/620 |
| 6,188,647 | B1 | | 2/2001 | Drumheller | 367/165 |
| 6,644,116 | B2 | | 11/2003 | Getman et al. | 73/290 |
| 2003/0010114 | A1 | | 1/2003 | Getman et al. | |
| 2010/0327700 | A1 | * | 12/2010 | Turner | 310/342 |
| 2011/0012480 | A1 | * | 1/2011 | Turner | 310/346 |

FOREIGN PATENT DOCUMENTS

| CN | 1423582 | 6/2003 |
| DE | 10 2004 033 311 A1 | 1/2006 |

(Continued)

OTHER PUBLICATIONS

Notification of Transmittal of the International Search Report and the Written Opinion of the International Searching authority, or the Declaration for PCT/US2009/001262 filed Feb. 27, 2009; 14 pages.

(Continued)

*Primary Examiner* — Derek Rosenau
(74) *Attorney, Agent, or Firm* — Westman, Champlin & Kelly, P.A.

(57) ABSTRACT

The invention describes a vibrating tine level detection device, and a method of forming the same, which is particularly suitable for operation in environments subject to rapid temperature change. A piezoelectric stack, which generates vibration of the tine, is located within a cage. The cage is, in turn, located within a hollow body defined by a diaphragm, from which the tines extend, and a wall section. The cage is attached to the inside surface of the wall section, adjacent to the junction between the wall section and the diaphragm. As a consequence, the ability of the cage to maintain a substantially constant compression on the piezoelectric stack is substantially unaffected by thermal expansion or contraction of the wall section.

9 Claims, 1 Drawing Sheet

FOREIGN PATENT DOCUMENTS

| | | |
|---|---|---|
| EP | 0810423 | 12/1997 |
| EP | 2 031 359 A1 | 3/2009 |
| GB | 2150292 | 10/1984 |
| GB | 2 351 805 A | 1/2001 |
| WO | WO0195667 | 12/2001 |
| WO | WO 2006/005660 | 1/2006 |

OTHER PUBLICATIONS

Second Chinese Office Action for Chinese Application No. 200980106981.5, dated Apr. 24, 2012, 2 pages.

First Chinese Office Action (with English translation) for corresponding Chinese patent application No. 200980106983.4, dated Feb. 13, 2012, 12 pages.

First Chinese Office Action for corresponding Chinese Application No. 200980107323.8, dated Feb. 13, 2012, 4 pages.

"Notification of Transmittal of the International Search Report and the Written Opinion of the International Search Authority" for PCT/US2009/001246, dated Jul. 28, 2009.

First Office Action (with English Translation) for Chinese Application No. 200980106981.5, dated Oct. 10, 2011, 10 pgs.

Search Report for PCT/US2009/001252, dated Jul. 6, 2009, 2 pgs.

Second Chinese Office Action for Chinese Application No. 200980106983.4, dated Nov. 29, 2012, 6 pages.

* cited by examiner

VIBRATING ELEMENT APPARATUS

CROSS-REFERENCE TO RELATED APPLICATION

This Application is a Section 371 National Stage Application of International Application No. PCT/US2009/001262, filed Feb. 27, 2009 and published as WO2009/110988 on Sep. 11, 2009, in English, the contents of which are hereby incorporated by reference in their entirety.

FIELD OF THE INVENTION

This invention relates to a novel vibrating element apparatus and has been devised, in particular, to provide a fluid level transducer for use in environments which are, or could be, subject to rapid temperature change. However, it will be appreciated by those skilled in the art, that the invention could also be applied to vibrating element apparatus configured to measure density and/or viscosity.

BACKGROUND

Various forms of apparatus including one or more vibrating elements are well known in the field of plant or process control, one example being a contact fluid level transducer. A typical contact fluid transducer includes a pair of spaced tines mounted on a diaphragm, the diaphragm in turn defining one end of a hollow cylindrical body. The tines are arranged to vibrate at a given frequency, typically their resonant frequency, and vibration is typically effected by displacing the centre of the diaphragm by means of a compressed stack of piezoelectric elements, located within the hollow body, and driven by a cycling voltage. When the vibrating tines come into contact with a fluid, there is a change in the frequency at which they vibrate. By detecting the change in frequency, one can determine when a rising fluid level contacts the tines. Likewise one can detect when a fluid level drops below the level of the tines.

An early example of this type of level detection device is described in UK Patent No. 2 150 292. In this device a stack of piezoelectric elements is compressed against the inner or reverse side of a diaphragm by a compression screw mounted in a bridge piece extending over that end of the stack remote from the diaphragm. The spaced tines extend from the outer or front side of the diaphragm, which diaphragm forms one end of a hollow body in which the piezoelectric stack is located. The bridge piece is, in turn, mounted on a pair of spaced rod-shaped supports extending from the inner side of the diaphragm and also located within the hollow body. When the piezoelectric stack is subjected to a cyclic drive voltage, the same expands and contracts between the compression screw and the diaphragm, deforming the diaphragm and causing the tines to vibrate.

It will be appreciated that the diaphragm must be relatively robust if it is to provide a mounting point for the rod shaped supports. This requirement runs counter to a general requirement that the diaphragm be relatively thin and thus require a minimum of energy to be applied to the piezoelectric elements in order to establish vibration of the tines.

A form of apparatus which addresses this latter requirement is shown in published International Patent Application No. WO 01/95667. In this device the piezoelectric stack is compressed against the inner surface of the diaphragm by a plug. The plug has a screw thread on its periphery which engages a corresponding screw thread provided on the inner surface of the hollow body. By rotating the plug relative to the hollow body, the compression on the piezoelectric stack can be established and, if necessary, adjusted. This arrangement performs perfectly well when the instrument is operating at normal ambient temperatures, however if the apparatus is subjected to a rapid change in temperature, the wall section, to which the diaphragm and plug are attached, will react to the change in temperature to a far greater extent that the components housed within the instrument. More particularly, if the environment is subjected to a sudden rise in temperature, the wall section will expand. This will cause the compressive force applied to the piezoelectric stack to be reduced, possibly to the extent that the instrument no longer functions. If the temperature of the environment lowers rapidly, the wall section will contract. This will increase the compressive force applied to the piezo stack and may damage the crystals by crushing. Alternatively, or in addition, the lower temperature may cause the components providing the clamping force to become over-stressed and loose their ability to maintain the required clamping force when the temperature increases once again.

The problem of a device of this type, subjected to rapid temperature change, is specifically addressed in U.S. Pat. No. 6,644,116. The device described in this patent incorporates a sleeve, spaced inwardly from the outer wall, to form a mount for the compression screw or plug. In one embodiment, the sleeve is mounted on the inner surface of the diaphragm and thus has the same drawbacks as are associated with UK 2 150 292 discussed above. In a second, preferred, embodiment the diaphragm and the outer wall are provided as separate components. A collar formed about one end of the sleeve is located between the diaphragm and the wall section and the three components are then welded together. This arrangement is effective at separating the compression screw from the expanding or contracting outer wall but, because the body itself is separated from the diaphragm, the inherent integrity of the body, which is defined by the wall/diaphragm unit, is lost and the resulting device must be subjected to pressure testing to ensure fitness for purpose.

It is an object of the present invention to address the above mentioned problems; or to provide a method and/or apparatus applicable to a level detection instrument, which will at least provide a novel and useful choice.

SUMMARY OF THE INVENTION

Accordingly, in one aspect, the invention provides a method of forming a vibrating element apparatus, said apparatus including:
a wall section having an inner surface and an outer surface;
a diaphragm formed integrally with, and closing one end of said wall section, said diaphragm having an inner surface and an outer surface, the inner surfaces of said wall section and said diaphragm defining a hollow body;
one or more vibrating elements extending from the outer surface of said diaphragm;
one or more piezoelectric elements located within said hollow body; and
a compression device operable to compress said one or more piezoelectric elements against the inner surface of said diaphragm;
said method being characterised in that a cage is provided which is locatable within said hollow body, inwardly spaced from said wall section, to serve as a mount for said compression device; and
said cage is fixed to the inner surface of said wall section adjacent to the junction between said wall section and said diaphragm.

Preferably said method further includes providing said cage with one or more fixing surface parts shaped to conform to said inner surface of said wall section.

Preferably said method still further includes configuring said cage so that, at assembly, said fixing surface parts are displaced against an inherent elasticity of said cage to allow said cage to be fitted within said hollow body.

Preferably said method includes spacing said cage from the inner surface of said diaphragm to ensure said cage does not interfere with the displacement of said diaphragm during movement of said one or more vibrating elements.

Preferably said cage is fixed to said wall section by a method selected from brazing, adhesive bonding, friction welding, resistance welding, spot welding, electron beam welding and laser beam welding; or a combination of more than one of these methods.

Alternatively said method includes retaining a suitably configured cage within a correspondingly configured wall section using a retaining ring or circlip.

In a second aspect the invention provides a vibrating element apparatus including:
a wall section having an inner surface and an outer surface;
a diaphragm formed integrally with, and closing one end of, said wall section, said diaphragm having an inner surface and an outer surface, the inner surfaces of said wall section and said diaphragm defining a hollow body;
one or more vibrating elements extending from the outer surface of said diaphragm;
one or more piezoelectric element located within said hollow body; and
a compression device operable to compress said one or more piezoelectric elements against the inner surface of said diaphragm;
said apparatus being characterised in that it includes a cage located within said hollow body, inwardly spaced from said wall section, to serve as a mount for said compression device, said cage being fixed to the inner surface of said wall section adjacent to the junction between said wall section and said diaphragm.

Preferably said cage includes one or more fixing surface parts shaped to conform to said inner surface of said wall section.

Preferably said fixing surface parts are defined on spaced legs, said legs projecting from a collar on or in which said compression device is included.

Preferably said cage has an inherent elasticity such that, at assembly, said fixing surface parts are elastically displaced to allow said cage to fit within said hollow body.

Preferably said cage is configured to locate and support said at least one piezoelectric element in relation to said diaphragm.

Preferably said at least one piezoelectric element is arranged in a stack comprising a plurality of piezoelectric elements, insulators and connectors.

Preferably said cage is spaced from the inner surface of said diaphragm to ensure said cage does not interfere with the displacement of said diaphragm during movement of said vibrating elements.

Preferably said one or more vibrating elements comprise a pair of tines.

Many variations in the way the invention may be performed will present themselves to those skilled in the art, upon reading the following description. The description should not be regarded as limiting but rather as an illustration, only, of one manner of performing the invention. Where appropriate any element or component should be taken as including any or all equivalents thereof whether or not specifically mentioned.

BRIEF DESCRIPTION OF THE DRAWINGS

One method of, and apparatus for, reducing the present invention to practice will now be described with reference to the accompanying drawings in which.

DETAILED DESCRIPTION OF WORKING EMBODIMENT

Figure 1:
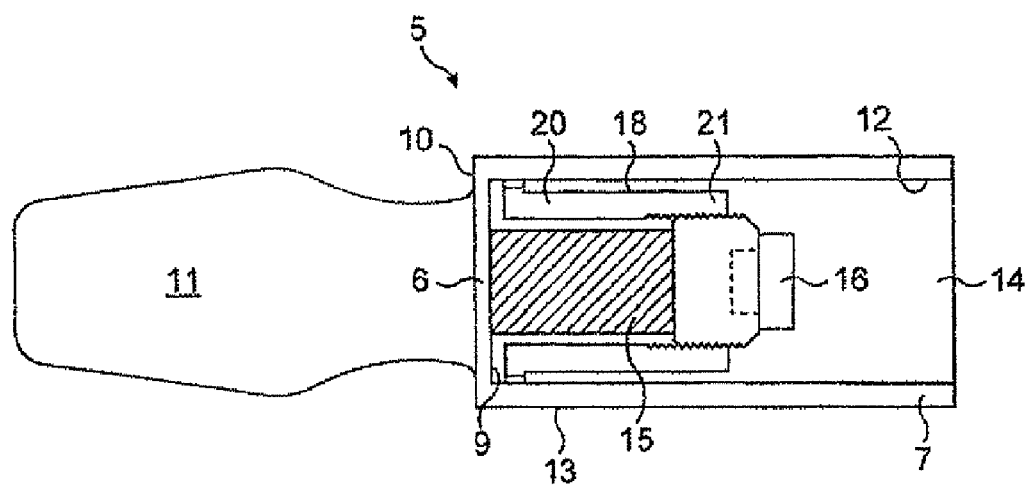
FIG. 1: shows a cross-section through a vibrating element apparatus according to the invention in the form of a liquid level detection transducer.

This invention provides a novel form of vibrating element apparatus which is, in the embodiment herein described, incorporated in a fork-type level fluid level transducer 5; and a method of forming the same. It will be appreciated, however, that a similarly configured device could also be used to measure density and/or viscosity.

In the known manner the apparatus 5 includes a diaphragm 6 integrally formed with, and closing one end of, a cylindrical wall section 7. The diaphragm has an inner surface 9 and an outer surface 10. A pair of tines, one of which is shown at 11, extends from the outer surface 10.

The wall section 7 has an inner surface 12 and an outer surface 13. The inner surface 9 of the diaphragm and the inner surface 12 of the wall section combine to define a hollow body 14.

Located in the hollow body 14 are one or more piezoelectric elements which, in combination with spacers, insulators, connectors and the like comprise a stack 15 which is held in compression against the inner surface 9 of the diaphragm by means of a compression device, preferably a compression screw 16. To the extent described thus far, the apparatus is entirely conventional. By applying a cycling voltage to the piezoelectric elements the diaphragm 6 is caused to cyclically deform and, in turn, cause the tines 11 to vibrate.

A characterising part of the invention is that the stack 15 is located within a cage 18 and the compression screw 16 is threadably mounted at that end of cage 18 remote from the diaphragm 6. It can be seen that the cage 18 is located within the hollow body 14 but inwardly of the inner surface 12 of the wall section 7 and is fixed to the inner surface 12 of wall section 7 adjacent to the junction between the diaphragm 6 and the wall section 7. As a result, axial expansion or contraction of the wall section 7, when subjected to rapid temperature changes, will not cause the compression on the piezoelectric stack 15 to vary to the extent that the apparatus ceases to function—either because the compression is reduced to a degree which does not allow the forks to vibrate, or increased to a level which crushes and destroys the piezoelectric elements, or over-stresses the components providing the compression.

Figure 2:
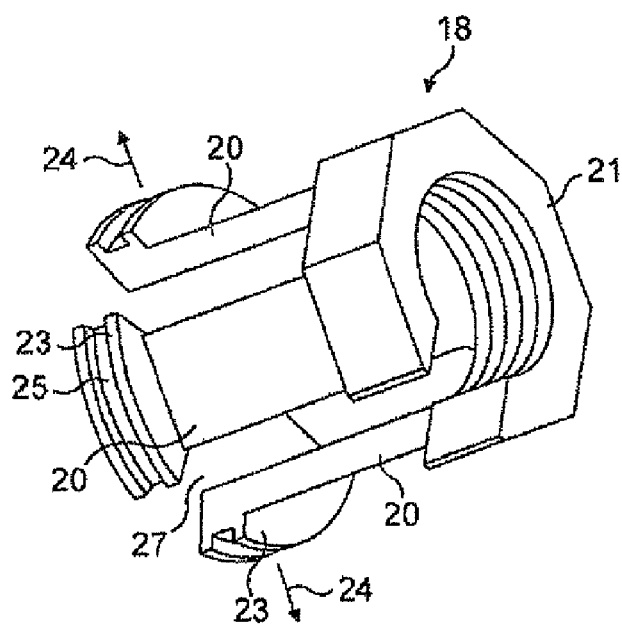
FIG. 2: shows an isometric view of a cage incorporated in the apparatus shown in FIG. 1.

Referring now to FIG. 2, the cage 18 is preferably defined by a plurality of legs 20 extending from one side of a common collar 21. Located at the distal end of each leg 20 is a fixing surface part 23, by means of which the cage is fixed to the inner surface 12 of the wall section 7. To that end it will be noted that each fixing surface part 23 has a curvature corresponding to the curvature of the inner surface 12.

In the embodiment depicted, four legs 20 are provided. This number is not critical though it is believed that an even number of legs is preferred to ensure a balanced loading on the vibrating structure. Each of the legs 20 is preferably splayed outwardly in the direction of arrows 24 so that, upon assembly the legs are displaced inwardly against an inherent elasticity of the cage to be assembled within the hollow body 14. Upon release of the displacing force, the legs recover towards their original configuration and, in so doing, centre the cage within the hollow body 14 and hold the cage 18 in position while fixing to the wall section 7 is effected. Alternatively the legs can be formed to fit easily within the hollow body 14 and, once the cage is in position within the body 14, be splayed outwardly into contact with the inner wall surface 12 by a suitable punch or jig.

The fixing parts 23 of the legs 20 may be fixed to the inner surface 12 of the wall section 7 by a number of methods including, but not necessarily limited to, brazing, adhesive bonding; friction welding, resistance welding, spot welding, electron beam welding and laser beam welding; or a combination of more than one of these. In the particular embodiment depicted, fixing is effected by brazing, particularly brazing using a vacuum brazing oven. A Ni or Cu based braze is preferably used. For example EN1044 type Ni 102 material, a version of which is NICROBRAZ LM from Wall-Colmonoy. This particular material is applied, in paste form, to grooves 25 provided in fixing surface parts 23. The cage is then assembled into the hollow body 14, preferably using a jig to ensure a small gap of around 1.5 mm is left between the cage and the inner surface 9 of diaphragm 6 to ensure the cage does not interfere with the vibration of the diaphragm. Once the cage is in place within the hollow body 14, the assembly is placed in a vacuum oven and heated to effect fixing. Using 316 grade stainless steel for both the wall section and the cage, and using Ni-based brazing compounds of the types identified, fixing is effected by heating to approximately 1040° C. and holding at this temperature for about 2 minutes.

It will be appreciated that the braze material could be provided in forms other than paste form. It could, for example, be provided in the form of a ring of wire. Other fixing materials could also be provided in forms which make their use most efficient and effective.

It is also envisaged that the cage might be fixed to the wall section by a mechanical connection. For example by use of a retaining ring or circlip on an appropriately configured cage and wall section.

Finally, it will be noted that the cage is preferably provided with a slot 27 which extends the fill length of the cage, including through the collar 21, to provide a passage for wires connecting the piezoelectric elements to the driver and processing electronics. Again this slot is not essential and the required clearance could also be achieved by a cut-out in the collar or by a bore or slot in the compression screw.

It will thus be appreciated that the present invention provides an effective form of tuning fork level detection transducer, and a method of forming the same, which is not only suitable for use in rapidly changing temperature environments but can also retain a suitably thin diaphragm while maintaining diaphragm/wall section integrity. A further benefit is that, because the invention does not involve any modification to the outer body, the same outer body and processing electronics as are used in prior art versions of level to detection transducer, can be used to implement this invention.

The invention claimed is:

1. A vibrating element apparatus including:
a wall section having inner surfaces and an outer surface;
a diaphragm formed integrally with, and closing one end of, said wall section, said diaphragm having an inner surface and an outer surface, the inner surfaces of said wall section and said diaphragm defining a hollow body;
one or more vibrating elements extending from the outer surface of said diaphragm;
one or more piezoelectric elements located within said hollow body; and
a compression device operable to compress said one or more piezoelectric elements against the inner surface of said diaphragm;
said apparatus being characterised in that it includes a separate cage located within said hollow body, inwardly spaced from said wall section, to serve as a mount for said compression device, said cage having a plurality of spaced legs which are splayed outwardly into contact with, and fixed to, the inner surface of said wall section adjacent to the junction between said wall section and said diaphragm.

2. Apparatus as claimed in claim 1 wherein each of said legs includes one or more fixing surface parts shaped to conform to said inner surface of said wall section.

3. Apparatus as claimed in claim 2 wherein said legs project from a collar on or in which said compression device is included.

4. Apparatus as claimed in claim 1 wherein said cage is configured to locate and support said at least one piezoelectric element in relation to said diaphragm.

5. Apparatus as claimed in claim 1 wherein said at least one piezoelectric element is mounted in a stack comprising a plurality of piezoelectric elements, insulators and connectors.

6. Apparatus as claimed in claim 1 wherein said cage is spaced from the inner surface of said diaphragm to ensure said cage does not interfere with the displacement of said diaphragm during movement of said one or more vibrating elements.

7. Apparatus as claimed in claim 1 wherein said one or more vibrating elements comprise a pair of tines.

8. A vibrating element apparatus including:
a wall section having an inner surface and an outer surface;
a diaphragm formed with, and closing one end of, said wall section, said diaphragm having an inner surface and an outer surface, the inner surfaces of said wall section and said diaphragm defining a seamless hollow body;
one or more vibrating elements extending from the outer surface of said diaphragm;
one or more piezoelectric elements located within said hollow body; and
a compression device operable to compress said one or more piezoelectric elements against the inner surface of said diaphragm;
said apparatus being characterised in that it includes a separate cage located within said hollow body, inwardly spaced from said wall section, to serve as a mount for said compression device, said cage having a plurality of spaced legs which are splayed outwardly into contact with, and fixed to, the inner surface of said wall section adjacent to the junction between said wall section and said diaphragm.

9. A vibrating element apparatus including:
a wall section having an inner surface and an outer surface;
a diaphragm formed with, and closing one end of, said wall section, said diaphragm having an inner surface and an outer surface, the inner surfaces of said wall section and said diaphragm defining a hollow body;
one or more vibrating elements extending from the outer surface of said diaphragm;
one or more piezoelectric elements located within said hollow body; and a compression device operable to compress said one or more piezoelectric elements against the inner surface of said diaphragm;

said apparatus being characterised in that it includes a separate cage located within said hollow body, inwardly spaced from said wall section, to serve as a mount for said compression device, said cage having a plurality of spaced legs which are splayed outwardly into contact with, and fixed to, the inner surface of said wall section adjacent to the junction between said wall section and said diaphragm such that the entirety of the spaced legs are within the hollow body.

* * * * *